United States Patent
Li et al.

(10) Patent No.: US 9,637,395 B2
(45) Date of Patent: May 2, 2017

(54) FLUORINE FREE TUNGSTEN ALD/CVD PROCESS

(71) Applicant: ENTEGRIS, INC., Billerica, MA (US)

(72) Inventors: Weimin Li, New Milford, CT (US);
David W. Peters, Burnet, TX (US);
Scott L. Battle, Cedar Park, TX (US);
William Hunks, Waterbury, CT (US)

(73) Assignee: Entegris, Inc., Billerica, MA (US)

( * ) Notice: Subject to any disclaimer, the term of this patent is extended or adjusted under 35 U.S.C. 154(b) by 0 days.

(21) Appl. No.: 14/431,116

(22) PCT Filed: Sep. 26, 2013

(86) PCT No.: PCT/US2013/061996
§ 371 (c)(1),
(2) Date: Mar. 25, 2015

(87) PCT Pub. No.: WO2014/052642
PCT Pub. Date: Apr. 3, 2014

(65) Prior Publication Data
US 2015/0251920 A1    Sep. 10, 2015

Related U.S. Application Data

(60) Provisional application No. 61/707,656, filed on Sep. 28, 2012.

(51) Int. Cl.
*C07F 11/00* (2006.01)
*C01G 41/00* (2006.01)
(Continued)

(52) U.S. Cl.
CPC ............ *C01G 41/006* (2013.01); *C01C 3/11* (2013.01); *C07F 11/00* (2013.01); *C07F 11/005* (2013.01);
(Continued)

(58) Field of Classification Search
None
See application file for complete search history.

(56) References Cited

U.S. PATENT DOCUMENTS 3,064,021 A    11/1962   Wilkinson, G.
4,726,961 A     2/1988   Diem et al.
(Continued)

FOREIGN PATENT DOCUMENTS

EP         1806352 B1    12/2010
KR   10-2006-0077768 A    7/2006
(Continued)

OTHER PUBLICATIONS

Schadt, Inorganic Chemistry, 1986, V25, p. 672-677.*
(Continued)

*Primary Examiner* — Joseph Miller, Jr.

(57) ABSTRACT

A tungsten precursor useful for forming tungsten-containing material on a substrate, e.g., in the manufacture of microelectronic devices. The tungsten precursor is devoid of fluorine content, and may be utilized in a solid delivery process or other vapor deposition technique, to form films such as elemental tungsten for metallization of integrated circuits, or tungsten nitride films or other tungsten compound films that are useful as base layers for subsequent elemental tungsten metallization.

9 Claims, 1 Drawing Sheet

(51) Int. Cl.
*C23C 16/16* (2006.01)
*C23C 16/18* (2006.01)
*C23C 16/448* (2006.01)
*C01C 3/11* (2006.01)
*C09D 5/24* (2006.01)
*H01B 1/02* (2006.01)

(52) U.S. Cl.
CPC ............... *C09D 5/24* (2013.01); *C23C 16/16* (2013.01); *C23C 16/18* (2013.01); *C23C 16/4485* (2013.01); *H01B 1/02* (2013.01)

(56) References Cited

U.S. PATENT DOCUMENTS

| | | | |
|---|---|---|---|
| 5,393,565 | A | 2/1995 | Suzuki et al. |
| 6,437,161 | B1 | 8/2002 | Mihan et al. |
| 6,884,466 | B2 | 4/2005 | Kaloyeros et al. |
| 7,270,848 | B2 | 9/2007 | Suzuki et al. |
| 7,638,645 | B2 | 12/2009 | Gordon et al. |
| 7,745,333 | B2 | 6/2010 | Lai et al. |
| 7,754,908 | B2 | 7/2010 | Reuter et al. |
| 8,367,546 | B2 | 2/2013 | Humayun et al. |
| 8,435,894 | B2 | 5/2013 | Chandrashekar et al. |
| 8,513,116 | B2 | 8/2013 | Khandelwal et al. |
| 2003/0203616 | A1* | 10/2003 | Chung .................... C23C 16/16 438/627 |
| 2004/0016401 | A1* | 1/2004 | Ignatiev .............. C23C 16/0209 118/718 |
| 2006/0046478 | A1 | 3/2006 | Lim |
| 2006/0115977 | A1* | 6/2006 | Kim .................. H01L 21/28556 438/622 |
| 2006/0125099 | A1 | 6/2006 | Gordon et al. |
| 2007/0160761 | A1 | 7/2007 | Reuter et al. |
| 2007/0202254 | A1 | 8/2007 | Ganguli et al. |
| 2009/0022891 | A1 | 1/2009 | Sakai et al. |
| 2011/0305922 | A1 | 12/2011 | Noell |
| 2012/0003833 | A1 | 1/2012 | Khandelwal et al. |

FOREIGN PATENT DOCUMENTS

| | | |
|---|---|---|
| WO | 0112641 A1 | 2/2001 |
| WO | 2013046155 A1 | 4/2013 |

OTHER PUBLICATIONS

Ammerlaan, J., et al., "Chemical vapour deposition of tungsten by H2 reduction of WCl6", "Applied Surface Science", 1991, pp. 24-29, vol. 53.

Atagi, L., et al., "Reactivity of the Tungsten Carbyne W (=CCH3)Cl(PMe3)4: Double Carbonylation Carbyne-Alkyne Complexes, and Stoichiometric Acetylene Metathesis", "J. Am. Chem. Soc.", 1992, pp. 9223-9224, vol. 114.

Bchir, O., et al., "Tungsten Allylimido Complexes Cl4(RCN)W(NC3H5) as Single-Source CVD Precursors for WNxCy Thin Films. Correlation of Precursor Fragmentation to Film Properties", "J. Am. Chem. Soc.", May 6, 2005, pp. 7825-7833, vol. 127.

Cayton, R., et al., "The Tungsten-Tungsten Triple Bond-18. Bridging and Terminal Allyl Ligands in Complexes of the Formula W2(R)2(NMe2)4, Where R=C3H5 and C4H7", "Polyhedron", 1992, pp. 3197-3210, vol. 11, No. 24.

Chisholm, M., et al., "The Tungsten-Tungsten Triple Bond. 6. Hexakis(N,N-dimethylcarbamato)ditungsten and Demethyltetrakis(N,N-diethylcarbamato)ditungsten. Structures and Dynamical Solution Behavior", "Inorganic Chemistry", 1977, pp. 603-611, vol. 16, No. 3.

Contreras, L., et al., "Seven-Coordinate Hydride Complexes of Molybdenum and Tungsten. Crystal and Molecular Structures of WH(Cl)(CO)2(PMe3)3", "Organometallics", 1993, pp. 4228-1233, vol. 12.

Dezelah, C., et al., "A low valent metalorganic precursor for the growth of tungsten nitride thin films by atomic layer deposition", "J. Mater. Chem.", Jan. 2, 2007, pp. 1109-1116, vol. 17.

Fowles, G., et al., "Reaction of some Aliphatic and Aromatic Nitriles with Tungsten(vi) Chloride leading to the Formation of Tungsten-Nitrogen multiply Bonded Compounds", "J. Chem. Soc., Dalton Trans.", 1977, pp. 1212-1214.

Gordon, R., et al., "Volatile Liquid Precursors for the Chemical Vapor Deposition (CVD) of Thin Films Containing Tungsten", "Mat. Res. Soc. Symp. Proc.", 2000, pp. D9.12.1-D9.12.6, vol. 612.

Hirose, F., et al., "Tungsten Deposition by Metal-Chloride-Reduction Chemical Vapor Deposition", "Electrochemical and Solid-State Letters", Apr. 7, 2011, pp. H251-H253, vol. 14, No. 7.

Kreickmann, T., et al., "Imido Alkylidene Bispyrrolyl Complexes of Tungsten", "Organometallics", Oct. 11, 2007, pp. 5702-5711, vol. 26.

Lai, K., et al., "Precursors for Organomettalic Chemical Vapor Deposition of Tungsten Carbide Films", "Chem. Mater.", 1995, pp. 2284-2292, vol. 7, No. 12.

Zinn, A. "Chapter 3: Chemical vapor deposition of tungsten", "The Chemistry of Metal CVD (Editors Kodas, T., et al.)", pp. 138, Copyright 1994, Published Online Dec. 26, 2007, Publisher: Wiley-VCH.

Note: For the non-patent literature citations that no month of publication is indicated, the year of publication is more than 1 year prior to the effective filing date of the present application.

Huo, C., et al, "Acetylene Hydroformylation with HCo(CO)3 as Catalyst. A Density Functional Study", Organometallics, Jan. 14, 2004, pp. 765-773, vol. 23.

Karolyi, B., et al, "Isonitrile ligand properties as studied by He I/He II photoelectron spectroscopy", Journal of Organometallic Chemistry, May 7, 2009, pp. 2923-2926, vol. 694.

Luo, X., et al., "The carbonyl insertion reaction of ethylCo(CO)n(PH3)4n and vinylCo(CO)n(PH3)4n: A detailed DFT study", Journal of Molecular Structure: THEOCHEM, Jun. 15, 2006, pp. 21-26, vol. 765.

* cited by examiner

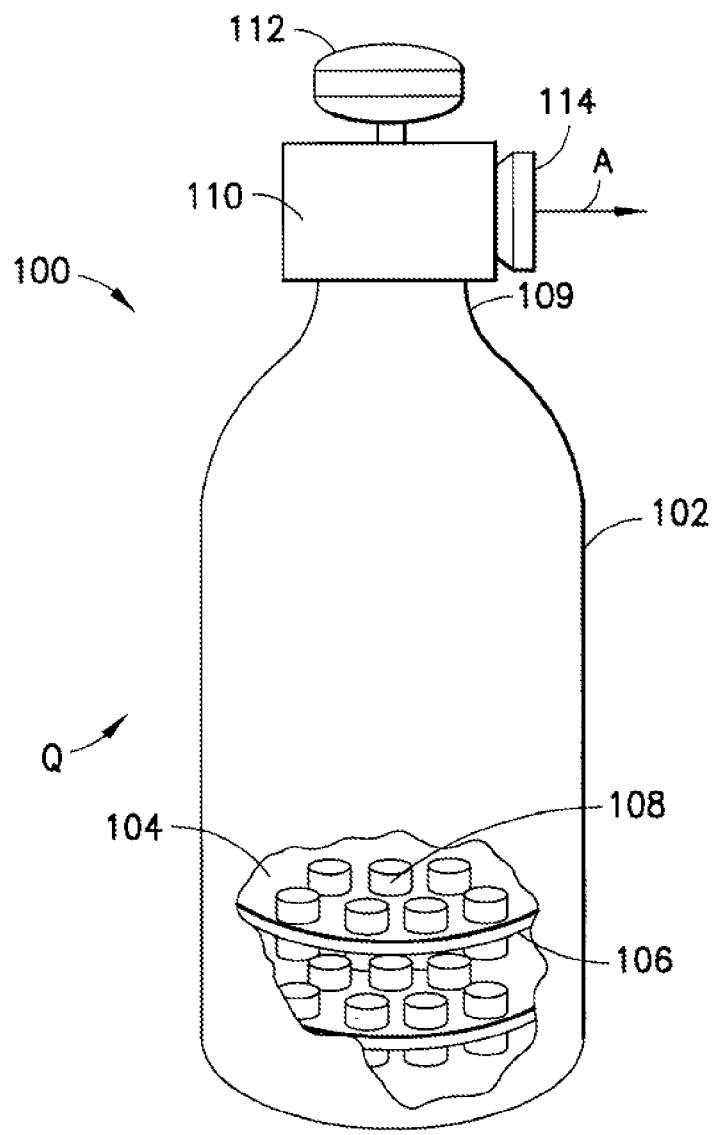

FLUORINE FREE TUNGSTEN ALD/CVD PROCESS

CROSS-REFERENCE TO RELATED APPLICATIONS

This application is a U.S. national phase under 35 USC 371 of International Patent Application No. PCT/US13/61996 filed Sep. 26, 2013, which in turn claims the benefit of priority under 35 USC 119 of U.S. Provisional Patent Application No. 61/707,656 filed Sep. 28, 2012 in the names of Weimin Li, et al. for FLUORINE FREE TUNGSTEN ALD/CVD PROCESS. The disclosures of such international patent application and U.S. Provisional Patent Application No. 61/707,656 are hereby incorporated herein by reference, in their respective entireties, for all purposes.

FIELD

The present disclosure relates to fluorine-free tungsten precursors for the deposition of tungsten-containing films on substrates, e.g., in the metallization of large-scale integrated circuits, as well as compositions comprising such precursors, and processes for making and using such precursors.

DESCRIPTION OF THE RELATED ART

In the manufacture of large-scale integrated circuits, the art continues to seek improved metallization reagents and processes. Tungsten has been utilized in such applications as a metallization material, e.g., as a plug filling medium for interlayer connections, as a result of its good electrical conductivity, high melting point, and high electric migration durability.

The conventional tungsten source reagent for such applications has been tungsten hexafluoride ($WF_6$). Tungsten hexafluoride, while generally useful as a precursor, has associated deficiencies that have motivated a search for alternative tungsten source reagents. These deficiencies of tungsten hexafluoride include interfacial consumption of silicon and corrosion of microelectronic devices deriving from hydrogen fluoride produced as a byproduct gas in the deposition of tungsten from tungsten hexafluoride.

It would therefore be desirable to provide new precursors for tungsten, which are desirably free of fluorine content to avoid the aforementioned deficiencies, and which exhibit good volatilization, transport and deposition properties for use in vapor deposition processes such as chemical vapor deposition (CVD) and atomic layer deposition (ALD).

SUMMARY

The present disclosure relates to fluorine-free tungsten precursors and compositions comprising same, as well as processes for making and using such precursors.

In one aspect, the disclosure relates to a tungsten precursor selected from the group consisting of:

(i) $WCl_xR_{6-x}$, wherein x is from 1 to 5, and R is selected from the group consisting of $C_1$-$C_8$ alkyl, $C_3$-$C_6$ cycloalkyl, $C_1$-$C_8$ alkoxy, cyano (nitrile), carbonyl, amino, alkylamino, dialkylamino, aryloxyalkyl, imidoalkyl, acetylalkyl, —$NR^aR^b$, $C(R^c)_3$, and —$Si(R^d)_3$, wherein each of $R^a$, $R^b$ and $R^c$ is independently selected from $C_1$-$C_8$ alkyl; and wherein each $R^d$ is independently selected from among H, $C_1$-$C_8$ alkyl, $C_5$-$C_{10}$ cycloalkyl, $C_6$-$C_{10}$ aryl, and —$Si(R^e)_3$ wherein each $R^e$ is independently selected from $C_1$-$C_8$ alkyl;

(ii) $(RCN)_2WCl_4$, wherein R is selected from the group consisting of $C_1$-$C_8$ alkyl, $C_3$-$C_6$ cycloalkyl, $C_1$-$C_8$ alkoxy, cyano (nitrile), carbonyl, amino, alkylamino, dialkylamino, aryloxyalkyl, imidoalkyl, acetylalkyl, —$NR^aR^b$, $C(R^c)_3$, and —$Si(R^d)_3$, wherein each of $R^a$, $R^b$ and $R^e$ is independently selected from $C_1$-$C_8$ alkyl; and wherein each $R^d$ is independently selected from among H, $C_1$-$C_8$ alkyl, $C_5$-$C_{10}$ cycloalkyl, $C_6$-$C_{10}$ aryl, and —$Si(R^e)_3$ wherein each $R^e$ is independently selected from $C_1$-$C_8$ alkyl;

(iii) $\{tBuN=CH\}W(CO)_4$, wherein tBu is tertiarybutyl;

(iv)
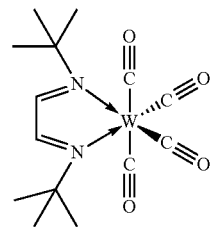

(v)
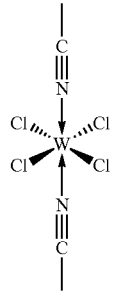

(vi) $WCl_4(PMe_3)_3$, wherein Me is methyl;
(vii) $WCl_4(DME)$, wherein DME is dimethoxyethane;
(viii) $\{tBuN=CH\}_2WCl_2$, wherein tBu is tertiarybutyl;
(ix) $\{tBuN=CH\}_2WCl_4$, wherein tBu is tertiarybutyl; and
(x) $WCl_3$-Q, wherein Q is an adduct moiety depositionally compatible with $WCl_3$; optionally further including one of:
(xi) $WCl_6$; and
(xii) $WCl_4$.

In another aspect, the disclosure relates to a method of forming tungsten or a tungsten-containing material on a substrate by chemical vapor deposition or atomic layer deposition, comprising use of a tungsten precursor of the present disclosure.

In a further aspect, the disclosure relates to a method of forming a tungsten or a tungsten-containing film on a substrate, comprising volatilizing a tungsten precursor of the present disclosure, to form a tungsten precursor vapor, and contacting the tungsten precursor vapor with a substrate under vapor deposition conditions, to form a the tungsten or tungsten-containing film on the substrate.

A further aspect of the disclosure relates to a process of forming a microelectronic device, comprising metallizing the device or a precursor structure thereof by a method as described above.

A still further aspect of the disclosure relates to a tungsten precursor supply package, comprising a vessel containing a tungsten precursor of the present disclosure.

Other aspects, features and embodiments of the disclosure will be more fully apparent from the ensuing description and appended claims.

BRIEF DESCRIPTION OF THE DRAWINGS

The FIGURE is a schematic representation of a material storage and dispensing package containing a tungsten precursor, according to one embodiment of the present disclosure.

DETAILED DESCRIPTION

The present disclosure relates to tungsten precursors that are free of fluorine content, as well as to compositions comprising such precursors, and to processes for making and using such precursors.

As used herein and in the appended claims, the singular forms "a", "and", and "the" include plural referents unless the context clearly dictates otherwise.

As used herein, the term "film" refers to a layer of deposited material having a thickness below 1000 micrometers, e.g., from such value down to atomic monolayer thickness values. In various embodiments, film thicknesses of deposited material layers in the practice of the invention may for example be below 100, 10, or 1 micrometers, or in various thin film regimes below 200, 100, or 50 nanometers, depending on the specific application involved. As used herein, the term "thin film" means a layer of a material having a thickness below 1 micrometer.

As used herein, the identification of a carbon number range, e.g., in $C_1$-$C_{12}$ alkyl, is intended to include each of the component carbon number moieties within such range, so that each intervening carbon number and any other stated or intervening carbon number value in that stated range, is encompassed, it being further understood that sub-ranges of carbon number within specified carbon number ranges may independently be included in smaller carbon number ranges, within the scope of the invention, and that ranges of carbon numbers specifically excluding a carbon number or numbers are included in the invention, and sub-ranges excluding either or both of carbon number limits of specified ranges are also included in the invention. Accordingly, $C_1$-$C_{12}$ alkyl is intended to include methyl, ethyl, propyl, butyl, pentyl, hexyl, heptyl, octyl, nonyl, decyl, undecyl and dodecyl, including straight chain as well as branched groups of such types. It therefore is to be appreciated that identification of a carbon number range, e.g., $C_1$-$C_{12}$, as broadly applicable to a substituent moiety, enables, in specific embodiments of the invention, the carbon number range to be further restricted, as a sub-group of moieties having a carbon number range within the broader specification of the substituent moiety. By way of example, the carbon number range e.g., $C_1$-$C_{12}$ alkyl, may be more restrictively specified, in particular embodiments of the invention, to encompass sub-ranges such as $C_1$-$C_4$ alkyl, $C_2$-$C_8$ alkyl, $C_2$-$C_4$ alkyl, $C_3$-$C_5$ alkyl, or any other sub-range within the broad carbon number range. In other words, a carbon number range is deemed to affirmatively set forth each of the carbon number species in the range, as to the substituent, moiety, or compound to which such range applies, as a selection group from which specific ones of the members of the selection group may be selected, either as a sequential carbon number sub-range, or as specific carbon number species within such selection group.

The same construction and selection flexibility is applicable to stoichiometric coefficients and numerical values specifying the number of atoms, functional groups, ions or moieties, as to specified ranges, numerical value constraints (e.g., inequalities, greater than, less than constraints), as well as oxidation states and other variables determinative of the specific form, charge state, and composition applicable to chemical entities within the broad scope of the present disclosure.

"Alkyls" as used herein include, but are not limited to, methyl, ethyl, propyl, isopropyl, butyl, s-butyl, t-butyl, pentyl and isopentyl and the like. "Aryls" as used herein includes hydrocarbons derived from benzene or a benzene derivative that are unsaturated aromatic carbocyclic groups of from 6 to 10 carbon atoms. The aryls may have a single or multiple rings. The term "aryl" as used herein also includes substituted aryls. Examples include, but are not limited to phenyl, naphthyl, xylene, phenylethane, substituted phenyl, substituted naphthyl, substituted xylene, substituted phenylethane and the like. "Cycloalkyls" as used herein include, but are not limited to cyclopropyl, cyclobutyl, cyclopentyl, cyclohexyl and the like. In all chemical formulae herein, a range of carbon numbers will be regarded as specifying a sequence of consecutive alternative carbon-containing moieties, including all moieties containing numbers of carbon atoms intermediate the endpoint values of carbon number in the specific range as well as moieties containing numbers of carbon atoms equal to an endpoint value of the specific range, e.g., $C_1$-$C_6$, is inclusive of $C_1$, $C_2$, $C_3$, $C_4$, $C_5$ and $C_6$, and each of such broader ranges may be further limitingly specified with reference to carbon numbers within such ranges, as sub-ranges thereof. Thus, for example, the range $C_1$-$C_6$ would be inclusive of and can be further limited by specification of sub-ranges such as $C_1$-$C_3$, $C_1$-$C_4$, $C_2$-$C_6$, $C_4$-$C_6$, etc. within the scope of the broader range.

The invention, as variously described herein in respect of features, aspects and embodiments thereof, may in particular implementations be constituted as comprising, consisting, or consisting essentially of, some or all of such features, aspects and embodiments, as well as elements and components thereof being aggregated to constitute various further implementations of the invention. The invention is described herein in various embodiments, and with reference to various features and aspects of the invention. The invention contemplates such features, aspects and embodiments in various permutations and combinations, as being within the scope of the invention. The invention may therefore be specified as comprising, consisting or consisting essentially of, any of such combinations and permutations of these specific features, aspects and embodiments, or a selected one or ones thereof.

As used herein, the term "depositionally compatible" in reference to an addict moiety means that such moiety is compatible with deposition of tungsten from the corresponding precursor in a vapor deposition process, so that the tungsten precursor including such adduct moiety is able to be volatilized, transported, and contacted with a substrate under vapor deposition conditions, to enable deposition of tungsten or tungsten-containing material on the substrate in a film.

The tungsten precursors of the present disclosure include tungsten precursors selected from the group consisting of:
(i) $WCl_xR_{6-x}$, wherein x is from 1 to 5, and R is selected from the group consisting of $C_1$-$C_8$ alkyl, $C_3$-$C_6$ cycloalkyl, $C_1$-$C_8$ alkoxy, cyano (nitrile), carbonyl, amino, alkylamino, dialkylamino, aryloxyalkyl, imidoalkyl, acetylalkyl, —$NR^aR^b$, $C(R^c)_3$, and —$Si(R^d)_3$, wherein each of $R^a$, $R^b$ and $R^c$ is independently selected from $C_1$-$C_8$ alkyl; and wherein each $R^d$ is independently selected from among H, $C_1$-$C_8$ alkyl, $C_5$-$C_{10}$ cycloalkyl, $C_6$-$C_{10}$ aryl, and —$Si(R^e)_3$ wherein each $R^e$ is independently selected from $C_1$-$C_8$ alkyl;

(ii) $(RCN)_2WCl_4$, wherein R is selected from the group consisting of $C_1$-$C_8$ alkyl, $C_3$-$C_6$ cycloalkyl, $C_1$-$C_8$ alkoxy, cyano (nitrile), carbonyl, amino, alkylamino, dialkylamino, aryloxyalkyl, imidoalkyl, acetylalkyl, $—NR^aR^b$, $C(R^c)_3$, and $—Si(R^d)_3$, wherein each of $R^a$, $R^b$ and $R^c$ is independently selected from $C_1$-$C_8$ alkyl; and wherein each $R^d$ is independently selected from among H, $C_1$-$C_8$ alkyl, $C_5$-$C_{10}$ cycloalkyl, $C_6$-$C_{10}$ aryl, and $—Si(R^e)_3$ wherein each $R^e$ is independently selected from $C_1$-$C_8$ alkyl;

(iii) $\{tBuN=CH\}W(CO)_4$, wherein tBu is tertiarybutyl;

(iv)

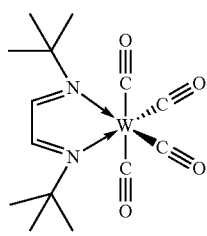

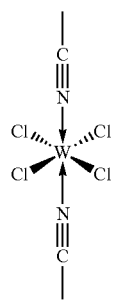

(vi) $WCl_4(PMe_3)_3$, wherein Me is methyl;
(vii) $WCl_4(DME)$, wherein DME is dimethoxyethane;
(viii) $\{tBuN=CH\}_2WCl_2$, wherein tBu is tertiarybutyl;
(ix) $\{tBuN=CH\}_2WCl_4$, wherein tBu is tertiarybutyl; and
(x) $WCl_3$-Q, wherein Q is an adduct moiety depositionally compatible with $WCl_3$; optionally further including one of:
(xi) $WCl_6$;
(xii) $WCl_4$;

When the tungsten precursor comprises $WCl_3$-Q, the addict moiety Q may be of any suitable type conferring depositional compatibility to the corresponding precursor. In specific embodiments, the adduct moiety Q may comprise a moiety selected from the group consisting of aminoalkyl, alkoxyalkyl, aryloxyalkyl, imidoalkyl, and acetylalkyl, having the following formulae:

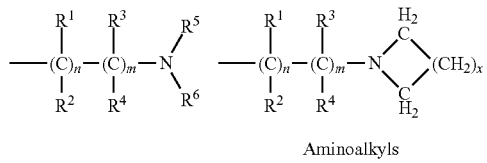

Aminoalkyls wherein: the methylene (—$CH_2$—) moiety could alternatively be another divalent hydrocarbyl moiety; each of $R^1$-$R^4$ is the same as or different from one another, with each being independently selected from among hydrogen, $C_1$-$C_6$ alkyl and $C_6$-$C_{10}$ aryl; each of $R^5$ and $R^6$ is the same as or different from the other, with each being independently selected from among hydrogen, $C_1$-$C_6$ alkyl; n and m are each selected independently as having a value of from 0 to 4, with the proviso that m and n cannot be 0 at the same time, and x is selected from 1 to 5;

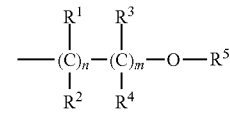

alkoxyalkyls and aryloxyalkyls wherein each of $R^1$-$R^4$ is the same as or different from one another, with each being independently selected from among hydrogen, $C_1$-$C_6$ alkyl, and $C_6$-$C_{10}$ aryl; $R^5$ is selected from among hydrogen, $C_1$-$C_6$ alkyl, and $C_6$-$C_{10}$ aryl; and n and m are selected independently as having a value of from 0 to 4, with the proviso that m and n cannot be 0 at the same time;

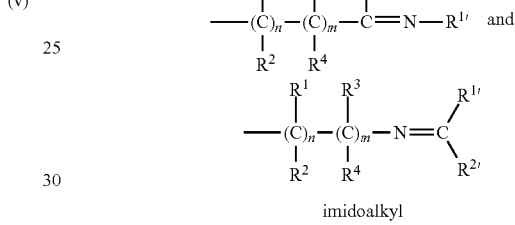

imidoalkyl wherein each of $R^1$, $R^2$, $R^3$, $R^4$, $R^5$ is the same as or different from one another, with each being independently selected from among hydrogen, $C_1$-$C_6$ alkyl, and $C_6$-$C_{10}$ aryl; each of $R^{1\prime}$, $R^{2\prime}$ is the same as or different from one another, with each being independently selected from hydrogen, $C_1$-$C_6$ alkyl, and $C_6$-$C_{10}$ aryl; and n and m are selected independently from 0 to 4, with the proviso that m and n cannot be 0 at the same time;

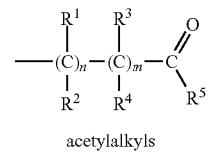

acetylalkyls wherein each of $R^1$-$R^4$ is the same as or different from one another, with each being independently selected from among hydrogen, $C_1$-$C_6$ alkyl, and $C_6$-$C_{10}$ aryl; $R^5$ is selected from among hydrogen, hydroxyl, acetoxy, $C_1$-$C_6$ alkyl, $C_1$-$C_{12}$ alkylamino, $C_6$-$C_{10}$ aryl, and $C_1$-$C_5$ alkoxy; and n and m are selected independently from 0 to 4, with the proviso that m and n cannot be 0 at the same time.

In some specific embodiments, the tungsten precursor contains no fluorine, carbon, oxygen, or nitrogen in the precursor molecule. Accordingly, the tungsten precursor may be a chlorotungsten compound or complex devoid of fluorine, carbon, oxygen, or nitrogen.

The present disclosure provides tungsten precursors that may be delivered by solid delivery techniques. For such purpose, the precursor may be provided in a vaporizer package, e.g., the solid vaporization package commercially available from ATMI, Inc. (Danbury, Conn., USA) under the trademark ProE-Vap, or other suitable vaporizer, in which the solid may be volatilized to form corresponding tungsten precursor vapor that then is transported by suitable flow circuitry to a deposition chamber in which the precursor vapor is contacted with a substrate to deposit tungsten thereon, either as elemental metal or as a tungsten-containing material, e.g., tungsten nitride, tungsten oxide, tungsten oxynitride, depending on the composition of the precursor vapor and the ambient environment under which the deposition is carried out.

Accordingly, the present disclosure contemplates a vapor deposition process in which a tungsten precursor of the disclosure is volatilized, transported to the deposition zone, and contacted with a substrate to deposit tungsten or tungsten-containing material thereon.

In various embodiments, the tungsten precursor can be employed in a deposition process in which the deposition conditions include a temperature of less than 300° C., e.g., a temperature in a range of from 150° C. to 200° C.

In other embodiments, the disclosure contemplates the formation of a nucleation layer comprising tungsten, by a deposition process including co-reactants such as ammonia or hydrogen, to form a corresponding tungsten nitride film or an elemental tungsten film, or both ammonia and hydrogen may be employed as a gas mixture that is flowed to the deposition chamber, e.g., either separately or in further mixture with the precursor vapor, to carry out the deposition and form a tungsten-containing film of desired character. The nucleation layer thickness in various embodiments may be less than 100 Å, or any other suitable thickness compatible with the subsequent deposition on the nucleation layer.

The vapor deposition process in which the tungsten precursor of the present disclosure is utilized to deposit tungsten or tungsten-containing material on a substrate may be of any suitable type. Potential vapor deposition processes that may be used in various implementations of the present disclosure include, without limitation, chemical vapor deposition (CVD), atomic layer deposition (ALD), pseudo-ALD, pulsed CVD, and plasma-enhanced or plasma-assisted CVD.

In a specific embodiment, tungsten is deposited by a solid delivery vapor deposition process using a tungsten precursor comprising tungsten hexachloride, and a hydrogen source. The hydrogen source may be ammonia, hydrogen, hydrogen plasma, ammonia plasma, a mixture of hydrogen and ammonia in plasma or non-plasma form, or a remote plasma hydrogen source. The tungsten may be deposited on a substrate over a suitable base layer (glue layer), e.g., of TiN, WN, TaN, TiAlN, TaAlN, TiTaN, etc.

The disclosure also contemplates forming a WN layer on a substrate, as a seed layer in situ, prior to tungsten deposition. The tungsten nitride layer may be formed on a glue layer such as titanium nitride, tantalum nitride, titanium aluminum nitride, or the like. Alternatively, the tungsten nitride layer may be formed directly on the substrate without any glue layer.

It will therefore be appreciated that the disclosure contemplates a wide variety of techniques and implementations for the deposition of tungsten-containing material on a substrate, e.g., in a film. The film may be of suitable thickness, and may comprise a thin film.

The disclosure correspondingly contemplates a method of manufacturing a microelectronic device, comprising metallizing a substrate with tungsten metallization from a tungsten precursor of the present disclosure, wherein the metallization is in the form of elemental tungsten or a tungsten composition (e.g., a tungsten alloy or other tungsten compound). Such metallizing may be utilized to provide interconnect structures, word or bit lines, or other structures of the microelectronic device or device precursor.

Tungsten precursors of the present disclosure can be readily synthesized within the skill of the art, based on the disclosure herein. Synthesis techniques for chlorotungsten precursors corresponding to those utilized in the manufacture of tungsten hexafluoride can be utilized, with corresponding chloro reagents in place of the fluoro agents utilized in such synthesis of $WF_6$, and with subsequent reaction in which the resulting chloro-functionalized tungsten compound is re-functionalized with other groups that are appropriately coordinated in the final chlorotungsten compound.

The disclosure in a further aspect relates to a material storage and dispensing package containing a tungsten precursor of the present disclosure.

The FIGURE is a schematic representation of a tungsten precursor storage and dispensing package 100 containing a tungsten precursor, according to one embodiment of the present disclosure.

The material storage and dispensing package 100 includes a vessel 102 that may for example be of generally cylindrical shape as illustrated, defining an interior volume 104 therein. In this embodiment, the tungsten precursor is a solid at ambient temperature conditions, and such precursor may be supported on surfaces of the trays 106 disposed in the interior volume 104 of the vessel, with the trays having flow passage conduits 108 associated therewith, for flow of vapor upwardly in the vessel to the valve head assembly, for dispensing in use of the vessel.

The solid precursor can be coated on interior surfaces in the interior volume of the vessel, e.g., on the surfaces of the trays 106 and conduits 108. Such coating may be effected by introduction of the precursor into the vessel in a vapor form from which the solid precursor is condensed in a film on the surfaces in the vessel. Alternatively, the precursor solid may be dissolved or suspended in a solvent medium and deposited on surfaces in the interior volume of the vessel by solvent evaporation. In yet another method the precursor may be melted and poured onto the surfaces in the interior volume of the vessel. For such purpose, the vessel may contain substrate articles or elements that provide additional surface area in the vessel for support of the precursor film thereon.

As a still further alternative, the solid precursor may be provided in granular or finely divided form, which is poured into the vessel to be retained on the top supporting surfaces of the respective trays 106 therein.

The vessel 102 has a neck portion 109 to which is joined the valve head assembly 110. The valve head assembly is equipped with a hand wheel 112 in the embodiment shown. The valve head assembly 110 includes a dispensing port 114, which may be configured for coupling to a fitting or connection element to join flow circuitry to the vessel. Such flow circuitry is schematically represented by arrow A in FIG. 1, and the flow circuitry may be coupled to a downstream ALD or chemical vapor deposition chamber (not shown in FIG. 1).

In use, the vessel 102 is heated, such input of heat being schematically shown by the reference arrow Q, so that solid precursor in the vessel is at least partially volatilized to provide precursor vapor. The precursor vapor is discharged from the vessel through the valve passages in the valve head assembly 110 when the hand wheel 112 is translated to an open valve position, whereupon vapor deriving from the precursor is dispensed into the flow circuitry schematically indicated by arrow A.

In lieu of solid delivery of the precursor, the precursor may be provided in a solvent medium, forming a solution or suspension. Such precursor-containing solvent composition then may be delivered by liquid delivery and flash vaporized to produce a precursor vapor. The precursor vapor is contacted with a substrate under deposition conditions, to deposit the metal on the substrate as a film thereon.

In one embodiment, the precursor is dissolved in an ionic liquid medium, from which precursor vapor is withdrawn from the ionic liquid solution under dispensing conditions.

It will be recognized that the tungsten precursors of the present disclosure may be packaged in a variety of suitable vessels for dispensing of precursor material to a downstream precursor-utilizing process tool or facility.

While the disclosure has been set out herein in reference to specific aspects, features and illustrative embodiments, it will be appreciated that the utility of the disclosure is not thus limited, but rather extends to and encompasses numerous other variations, modifications and alternative embodiments, as will suggest themselves to those of ordinary skill in the field of the present disclosure, based on the description herein. Correspondingly, the invention as hereinafter claimed is intended to be broadly construed and interpreted, as including all such variations, modifications and alternative embodiments, within its spirit and scope.

What is claimed is:

1. A method of forming a tungsten or a tungsten-containing film on a substrate comprising:
    providing a tungsten precursor,
    volatilizing the tungsten precursor to form a tungsten precursor vapor, and
    contacting the tungsten precursor vapor with a substrate under vapor deposition conditions to form the tungsten or tungsten-containing film on the substrate,
wherein the tungsten precursor comprises a tungsten precursor of the formula

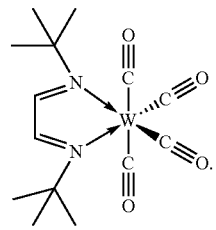

2. The method of claim 1, wherein the tungsten precursor further comprises $WCl_6$ or $WCl_4$.

3. The method of claim 1, wherein the tungsten precursor is provided in a solid form.

4. The method of claim 3, wherein the tungsten precursor is in particulate form.

5. The method of claim 3, wherein the tungsten precursor is coated on an interior surface in the vessel.

6. The method of claim 1, wherein the tungsten precursor is provided in a solvent medium.

7. The method of claim 6, wherein the tungsten precursor is provided in a solution.

8. The method of claim 6, wherein the tungsten precursor is provided in a suspension.

9. The method of claim 1, wherein the substrate comprises a glue layer of a material compatible with the tungsten or tungsten-containing film.

* * * * *